United States Patent [19]

Matsuo et al.

[11] Patent Number: 5,118,615

[45] Date of Patent: Jun. 2, 1992

[54] PEPTIDE AND GENE CODING FOR SAME

[75] Inventors: Hisayuki Matsuo; Kenji Kangawa, both of Miyazaki; Yujiro Hayashi, Neyagawa; Shinzo Oikawa, Kyoto; Takehiro Oshima, Takatsuki; Shoji Tanaka, Suita; Hiroshi Nakazato; Yasunori Tawaragi, both of Ibaraki, all of Japan

[73] Assignee: Suntory Limited, Osaka, Japan

[21] Appl. No.: 23,818

[22] Filed: Mar. 9, 1987

Related U.S. Application Data

[63] Continuation of Ser. No. 739,901, May 31, 1985, abandoned.

[30] Foreign Application Priority Data

| Jun. 8, 1984 [JP] | Japan | 59-116605 |
| Jun. 8, 1984 [JP] | Japan | 59-116606 |

[51] Int. Cl.⁵ .............. A61K 37/02; C12P 21/00; C12N 15/00; C12N 15/12; C07K 7/14

[52] U.S. Cl. .................. 435/69.1; 435/252.3; 435/320.1; 435/252.33; 536/27; 514/12; 514/869

[58] Field of Search .......... 435/68, 70, 91, 172.3, 435/635, 240, 253, 317; 536/27; 514/11-14, 929; 530/306, 324.26, 344, 353, 341; 935/11, 12, 29, 30, 38, 56, 60

[56] References Cited

U.S. PATENT DOCUMENTS

| 4,508,712 | 1/1985 | Needleman | 514/11 |
| 4,656,158 | 4/1987 | Matsuo et al. | 514/12 |
| 4,657,891 | 4/1987 | Matsuo et al. | 514/11 |
| 4,851,349 | 7/1989 | Nakanishi et al. | 435/252.33 |

FOREIGN PATENT DOCUMENTS 0116784 8/1984 European Pat. Off.
WO85/04870 11/1985 PCT Int'l Appl.

OTHER PUBLICATIONS

Nature, vol. 312, No. 5990, pp. 152-155 (Nov. 8, 1984)-Identification of rat γ atrial natriuretic polypeptide and characterization of the cDNA encoding its precursor.

Seidman, C. E., "The Structure of Rat Preproatrial Natriuretic Factor as Defined by a Complementary DNA Clone", Science, vol. 225, pp. 324-326 (1984).

Oikawa, S. et al, "Cloning and Sequence Analysis of cDNA Encoding a Precursor for Human Atrial Natriuretic Polypeptide", Nature, vol. 309, pp. 724-726 (1984).

Seidman, C. E. et al, "Nucleotide Sequences of the Human and Mouse Atrial Natriuretic Factor Genes", Science, vol. 226, pp. 1206-1209 (1984).

Yamanaka, M. et al, "Cloning and Sequence Analysis of the cDNA for the Rat Atrial Natriuretic Factor Precursor", Nature, vol. 309, pp. 719-722 (1984).

Maki, M. et al, "Structure of Rat Atrial Natriuretic Factor Precursor Deduced from cDNA Sequence", Nature, vol. 309, pp. 722-724 (1984).

Anderson et al. (1983) PNAS 80: 6838-42.
Helfman et al. (1983) PNAS 80: 31-5.
Currie (1983) Science 221:71-3.
Currie (1984) Science 223:67-9.
Backman (1978) Cell 13: 65-71.

Primary Examiner—Richard A. Schwartz
Assistant Examiner—S. L. Nolan
Attorney, Agent, or Firm—Burns, Doane, Swecker & Mathis

[57] ABSTRACT

Disclosed is a DNA fragment comprising a base sequence coding for a peptide occurring in human atrium cordis and having diuretic action or a precursor of the peptide, plasmids containing the DNA fragment, microorganisms transformed with the plasmid, and a process for production of the peptide using the transformant.

Also disclosed is a new peptide consisting of 126 amino acids occurring in human atrium cordis and a precursor thereof. The peptide has notable diuretic action and hypotensive or antihypertensive actions.

21 Claims, 15 Drawing Sheets

Fig. 1

```
Asn Pro Met Tyr Asn Ala Val Ser Asn Ala Asp Leu Met Asp Phe Lys Asn Leu Leu Asp
                                    10                                      20
His Leu Glu Glu Lys Met Pro Leu Glu Asp Glu Val Val Pro Gln Val Leu Ser Glu
                                    30                                      40
Pro Asn Glu Glu Ala Gly Ala Ala Leu Ser Pro Leu Pro Glu Val Pro Pro Trp Thr Gly
                                    50                                      60
Glu Val Ser Pro Ala Gln Arg Asp Gly Gly Ala Leu Gly Arg Gly Pro Try Asp Ser Ser
                                    70                                      80
Asp Arg Ser Ala Leu Leu Lys Ser Lys Leu Arg Ala Leu Leu Thr Ala Pro Arg Ser Leu
                                    90                                      100
Arg Arg Ser Ser Cys Phe Gly Gly Arg Met Asp Arg Ile Gly Ala Gln Ser Gly Leu Gly
                                    110                                     120
Cys Asn Ser Phe Arg Tyr
                126
```

Fig. 2

```
1                                           10                                          20
Met Ser Ser Phe Ser Thr Thr Thr Val Ser Phe Leu Leu Leu Ala Phe Gln Leu Leu 30                                          40
Gly Gln Thr Arg Ala Asn Pro Met Tyr Asn Ala Val Ser Asn Ala Asp Leu Met Asp Phe 50                                          60
Lys Asn Leu Leu Asp His Leu Glu Glu Lys Met Pro Leu Glu Asp Glu Val Val Pro Pro 70                                          80
Gln Val Leu Ser Glu Pro Asn Glu Glu Ala Gly Ala Ala Leu Ser Pro Leu Pro Glu Val 90                                          100
Pro Pro Trp Thr Gly Glu Val Ser Pro Ala Gln Arg Asp Gly Gly Ala Leu Gly Arg Gly 110                                         120
Pro Trp Asp Ser Ser Asp Arg Ser Ala Leu Leu Lys Ser Lys Leu Arg Ala Leu Leu Thr 130                                         140
Ala Pro Arg Ser Leu Arg Arg Arg Ser Ser Cys Phe Gly Gly Arg Met Asp Arg Ile Gly Ala

150
Gln Ser Gly Leu Gly Cys Asn Ser Phe Arg Tyr
```

Fig. 3

```
                                                       10                           20
AAT CCC ATG TAC AAT GCC GTG TCC AAC GCA GAC CTG ATG GAT TTC AAG AAT TTG CTG GAC
                                                       30                           40
CAT TTG GAA GAA AAG ATG CCT TTA GAA GAT GAG GTC GTG CCC CCA CAA GTG CTC AGT GAG
                                                       50                           60
CCG AAT GAA GAA GCG GGG GCT GCT CTC AGC CCC CTC CCT GAG GTG CCT CCC TGG ACC GGG
                                                       70                           80
GAA GTC AGC CCA GCC CAG AGA GAT GGA GGT GCC CTC GGG CGG GGC CCC TGG GAC TCC TCT
                                                       90                          100
GAT CGA TCT GCC CTC CTA AAA AGC AAG CTG AGG GCG CTG CTC ACT GCC CCT CGG AGC CTG
                                                      110                          120
CGG AGA TCC AGC TGC TTC GGG GGC AGG ATG GAC AGG ATT GGA GCC CAG AGC GGA CTG GGC
                    126
TGT AAC AGC TTC CGG TAC
```

Fig. 4

```
1                                   10                              20
ATG AGC TCC TTC TCC ACC ACC GTG AGC TTC CTC CTT TTA CTG GCA TTC CAG CTC CTA
                                    30                              40
GGT CAG ACC AGA GCT AAT CCC ATG TAC AAT GCC GTG TCC AAC GCA GAC CTG ATG GAT TTC
                                    50                              60
AAG AAT TTG CTG GAC CAT TTG GAA GAA AAG ATG CCT TTA GAA GAT GAG GTC GTG CCC CCA
                                    70                              80
CAA GTG CTC AGT GAG CCG AAT GAA GAA GCG GGG GCT GCT CTC AGC CCC CTC CCT GAG GTG
                                    90                              100
CCT CCC TGG ACC GGG GAA GTC AGC GCC CAG AGA GAT GGA GGT GCC CTC GGG CGG GGC
                                    110                             120
CCC TGG GAC TCC TCT GAT CGA TCT GCC CTC CTA AAA AGC AAG CTG AGG GCG CTG CTC ACT
                                    130                             140
GCC CCT CGG AGC CTG CGG AGA TCC AGC TGC TTC GGG GGC AGG ATG GAC AGG ATT GGA GCC
                                    150
CAG AGC GGA CTG GGC TGT AAC AGC TTC CGG TAC
```

Fig. 5

| Fig. 5A |
|---------|
| Fig. 5B |

Fig. 5A

```
                                                                                      -90
                                                                             5'-ACAGACGTAGG   -80

CCAAGAGAGGGGAACCAGAGAGACAGAGAGGAACCAGAGGGGAGAGACAGAGCAGCAAGCAGTGGATTGCTCCTTGACGACGCCAGC    -1

1                              10                           20
Met Ser Ser Phe Ser Thr Thr Val Ser Phe Leu Leu Leu Ala Phe Gln Leu Leu
ATG AGC TCC TTC TCC ACC ACC GTG AGC TTC CTC CTT TTA CTG GCA TTC CAG CTC CTA         60

30                             40
Gly Gln Thr Arg Ala Asn Pro Met Tyr Asn Ala Val Ser Asn Ala Asp Leu Met Asp Phe
GGT CAG ACC AGA GCT AAT CCC ATG TAC AAT GCC GTG TCC AAC GCA GAC CTG ATG GAT TTC   120

50                             60
Lys Asn Leu Leu Asp His Leu Glu Glu Lys Met Pro Leu Glu Asp Glu Val Val Pro Pro
AAG AAT TTG CTG GAC CAT TTG GAA GAA AAG ATG CCT TTA GAA GAT GAG GTC GTG CCC CCA   180

70                             80
Gln Val Leu Ser Glu Pro Asn Glu Glu Ala Gly Ala Ala Leu Ser Pro Leu Pro Glu Val
CAA GTG CTC AGT GAG CCG AAT GAA GAA GGG GCT GCT CTC AGC CCC CTC CCT GAG GTG        240
```

Fig.5B

```
          90                        100
Pro Pro Trp Thr Gly Glu Val Ser Pro Ala Gln Arg Asp Gly Gly Ala Leu Gly Arg Gly
CCT CCC TGG ACC GGG GAA GTC AGC CCA GCC CAG AGA GAT GGA GCT GCC CTC GGG CGG GGC    300

110                        120
Pro Trp Asp Ser Ser Asp Arg Ser Ala Leu Leu Lys Ser Lys Leu Arg Ala Leu Leu Thr
CCC TGG GAC TCC TCT GAT CGA TCT GCC CTC CTA AAA AGC AAG CTG AGG GCG CTG CTC ACT    360

130                        140
Ala Pro Arg Ser Leu Arg Arg Ser Ser Cys Phe Gly Gly Arg Met Asp Arg Ile Gly Ala
GCC CCT CGG AGC CTG CGG AGA TCC AGC TGC TTC GGG GGC AGG ATG GAC AGG ATT GGA GCC    420

150
Gln Ser Gly Leu Gly Cys Asn Ser Phe Arg Try
CAG AGC GGA CTG GGC TGT AAC AGC TTC CGG TAC TGA AGATAACAGCCAGGGAGGAGGACAAGCCAGGGCTG    487

GGCCTAGGGACAGAGACTGCAAGAGAGGCTCCTCCTGTCCCCTGGGGTCTCCTGCTGCTCTCTGTCATCTTGTTGCCATGGAGTTG    566

TGATCATCCCATCTAAGCTGCAGCTTCCTGTCAACACTTCTCACATCTTATGCTAACTGTAGATAAAGTGGTTTGATGG    645

TGACTTCCTCCGCCTCCCCACCCCATGCATTAAATTTTAAGGTAGAACCTCACCCTGTTACTGAAAGTGGTTTGAAAGTG    724

AATAAACTTCAGCACCATGGACAGAAGAC-3'    753
```

Fig. 9
Met Asp Arg Ile Gly
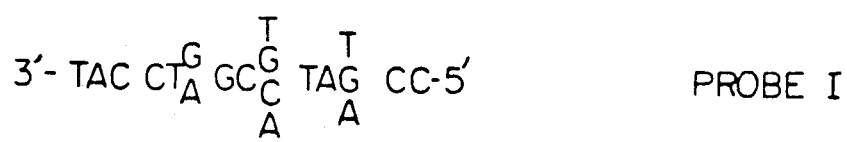
PROBE I
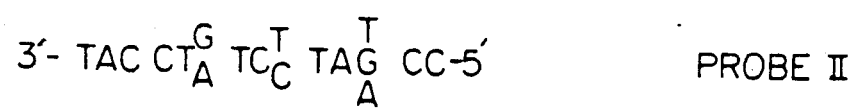
PROBE II
Fig. 12
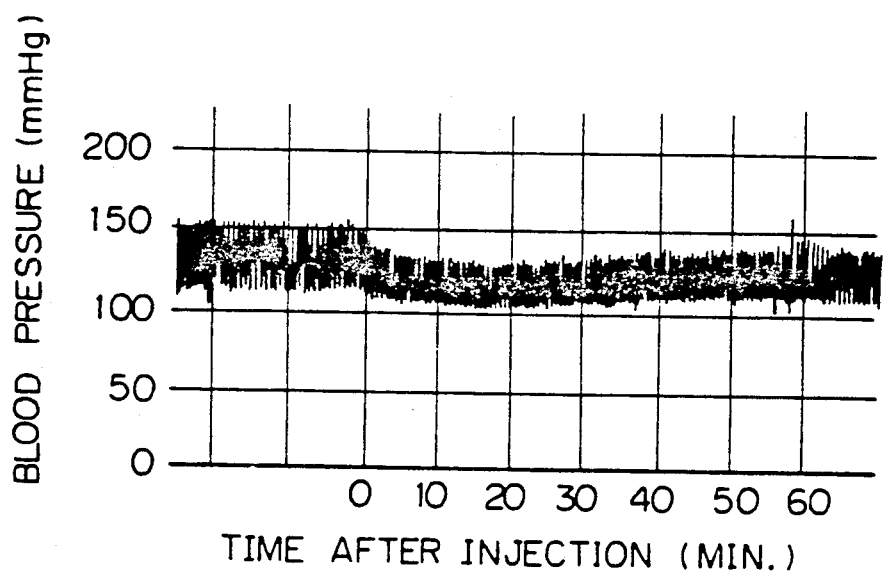

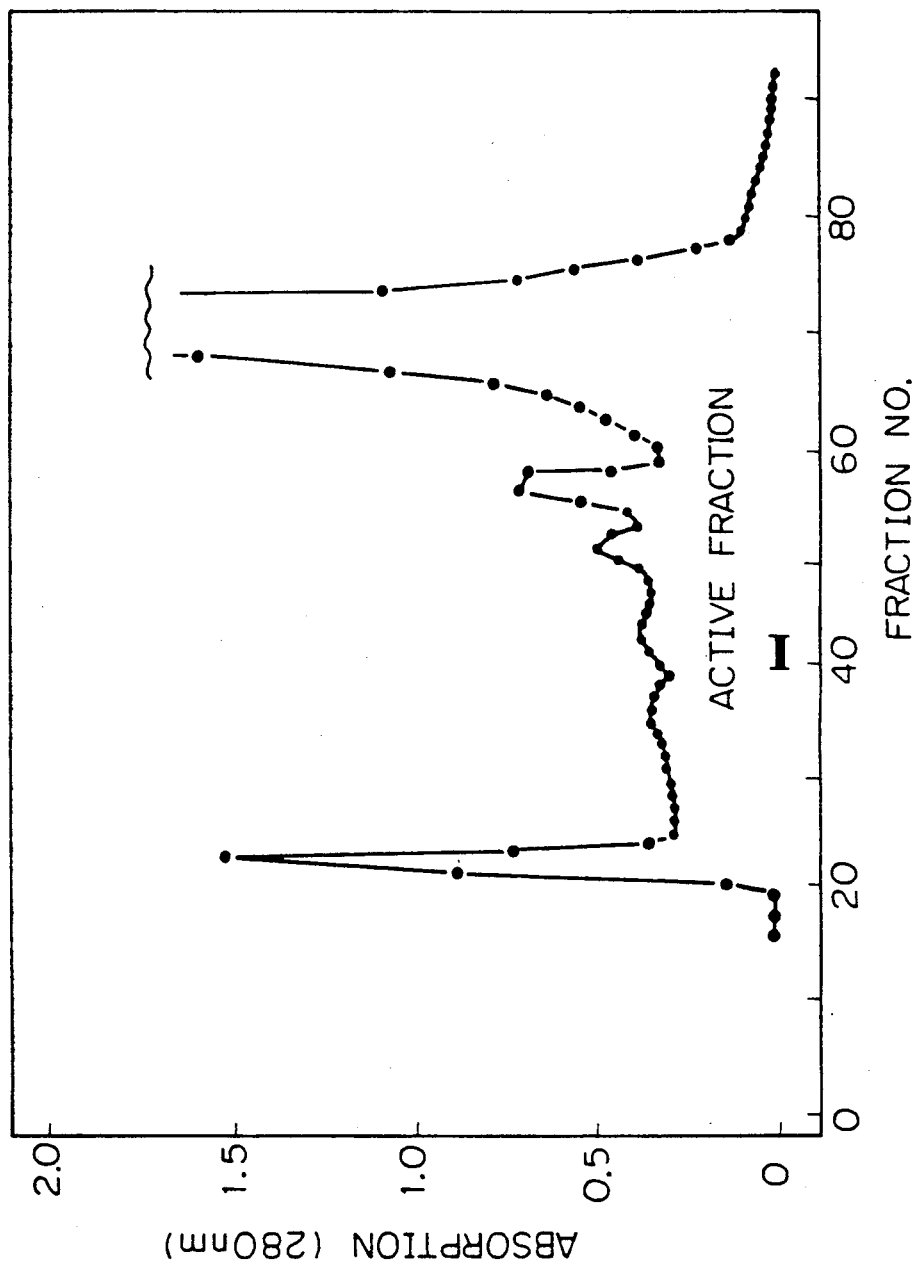

PEPTIDE AND GENE CODING FOR SAME

This application is a continuation of application Ser. No. 739,901, filed May 31, 1985 now abandoned.

BACKGROUND OF THE INVENTION

1. Field of the Invention

The present invention relates to a novel peptide, a gene coding for the peptide, a process for production of the peptide using the gene inserted to an expression vector, and use of the peptide.

2. Description of the Related Art

A normal regulation of the blood pressure in a human body is important for the maintenance of personal health, and various physical and humoral factors contribute to this regulation of the blood vessels, etc. The humoral factors include, for example, the reninangiotensin-aldosterone system, catecholamines, prostaglandins, kinin-kallikrein system, and natriuretic hormones including ouabain-like substances. Herein the term "natriuretic" will denote selective excretion of sodium cation relating to potassium cation.

Granules morphologically similar to granules present in peptide hormone-producing cells are found in human atrium (J.D. Jamieson and G.E. Palade, *J. Cell Biol.*, 23, 151, 1964). An extract of rat atrium and granules contained therein are known to show natriuretic action in rats (A.J. DeBold et. al., *Life Science*, 28, 89, 1981; R. Keeler, *Can. J. Physiol. Pharmacol.*, 60, 1078, 1982). Recently Mark G. Currie et. al. suggested peptide-like substances with a molecular weight of 20,000 to 30,000, or not more than 10,000, present in the atrium of humans, rabbits, swine, and rats, and having natriuretic action (Science, 221, 71–73, 1983).

Moreover, a peptide consisting of 28 amino acids derived from rat atrium cordis was identified (*Biochem. Biophys. Res. Commun.*; vol 117, No. 3, P859-865, 1983). The present inventors found a new peptide consisting of 28 amino acids from human atrium cordis, referred to as "α-human atrial natriuretic polypeptide" and abbreviated as "α-hANP" (*Biochem. Biophys. Res. Commun.* Vol 118, No. 1, P 131-139, 1984, U.S. Ser. No. 685151 of the present inventors. The α-hANP has following amino acid sequence:

```
      1                                             10
H—Ser—Leu—Arg—Arg—Ser—Ser—Cys—Phe—Gly—Gly—Arg—Met—

20
Asp—Arg—Ile—Gly—Ala—Glu—Ser—Gly—Leu—Gly—Cys—Asn—

28
Ser—Phe—Arg—Tyr—OH
``` wherein Cys at the 7 position and Cys at the 23 position are bonded through a disulfide bond.

Various kinds of physiologically active peptides are known to be derived in vivo from their precursors by the action of an endopeptidase or exopeptidase, rather than produced directly. For example, β-endorphin and γ-lipotropin are derived from their precursor β-lipotropin, and β-melanocyte-stimulating hormone is derived from its precursor γ-lipotropin (Takahashi H. et. al., FEBS Lett. 135, 97-102, 1981).

SUMMARY OF THE INVENTION

On the basis of the above-mentioned findings, the present inventors expected that the above-mentioned α-hANP would be derived from its precursor, and actually found a new peptide derived from human atrium cordis consisting of 126 amino acids including 28 amino acids of the α-hANP. Moreover, the present inventors successfully obtained a gene coding for the new peptide, and constructed plasmid containing the gene which expresses in a microorganism.

Therefore, the present invention provides a new peptide consisting of 126 amino acids and having diuretic action and hypotensive or antihypertensive action. The peptide is hereinafter referred to as "γ-human atrial natriuretic polypeptide" and abbreviated as γ-hANP".

There is also provided a DNA fragment comprising a base sequence coding for a peptide occurring in human atrium cordis and having diuretic action or a precursor of the peptide.

There is also provided plasmids containing a promotor region, SD sequence, and the above-mentioned DNA fragment, and capable of producing a peptide coded by the DNA fragment in a microorganism.

There is also provided a microorganism transformed with the plasmid.

Another object of the present invention is to provide a process for the production of the γ-hANP by culturing the transformed microorganism in a culture medium and recovering the γ-hANP from the cultured cells or medium.

Another object of the present invention is to provide a pharmaceutical composition containing the γ-hANP as a diuretic or hypotensor.

Other objects and advantages of the present invention will be apparent from the description set forth hereinbelow.

BRIEF DESCRIPTION OF THE DRAWINGS

FIG. 1 represents an amino acid sequence of γ-hANP consisting of 126 amino acids;

FIG. 2 represents an amino acid sequence of a precursor of the γ-hANP, which sequence consists of 151 amino acids wherein a sequence of from 26 to 151 corresponds to the sequence of the γ-hANP set forth in FIG. 1;

FIG. 3 represents a base sequence coding for the amino acid sequence set forth in FIG. 1;

FIG. 4 represents a base sequence coding for the amino acid sequence set forth in FIG. 2;

FIGS. 5a and 5b represent a sequence of a cDNA fragment cloned into plasmid phANP82 including a 5' non-coding region, a coding region corresponding to the base sequence set forth in FIG. 4, and a 3' non-coding region;

FIG. 9 represents base sequences of probes used for selection of DNA fragments coding for amino acid sequence of γ-hANP;

FIG. 12 represents a chart showing the hypotensive action of the γ-hANP;

FIG. 13 represents a chromatogram showing an elution profile using Sephadex G-75 during the purification of the γ-hANP;

DESCRIPTION OF THE PREFERRED EMBODIMENT

1. Identification of γ-hANP Gene

Figure 6:
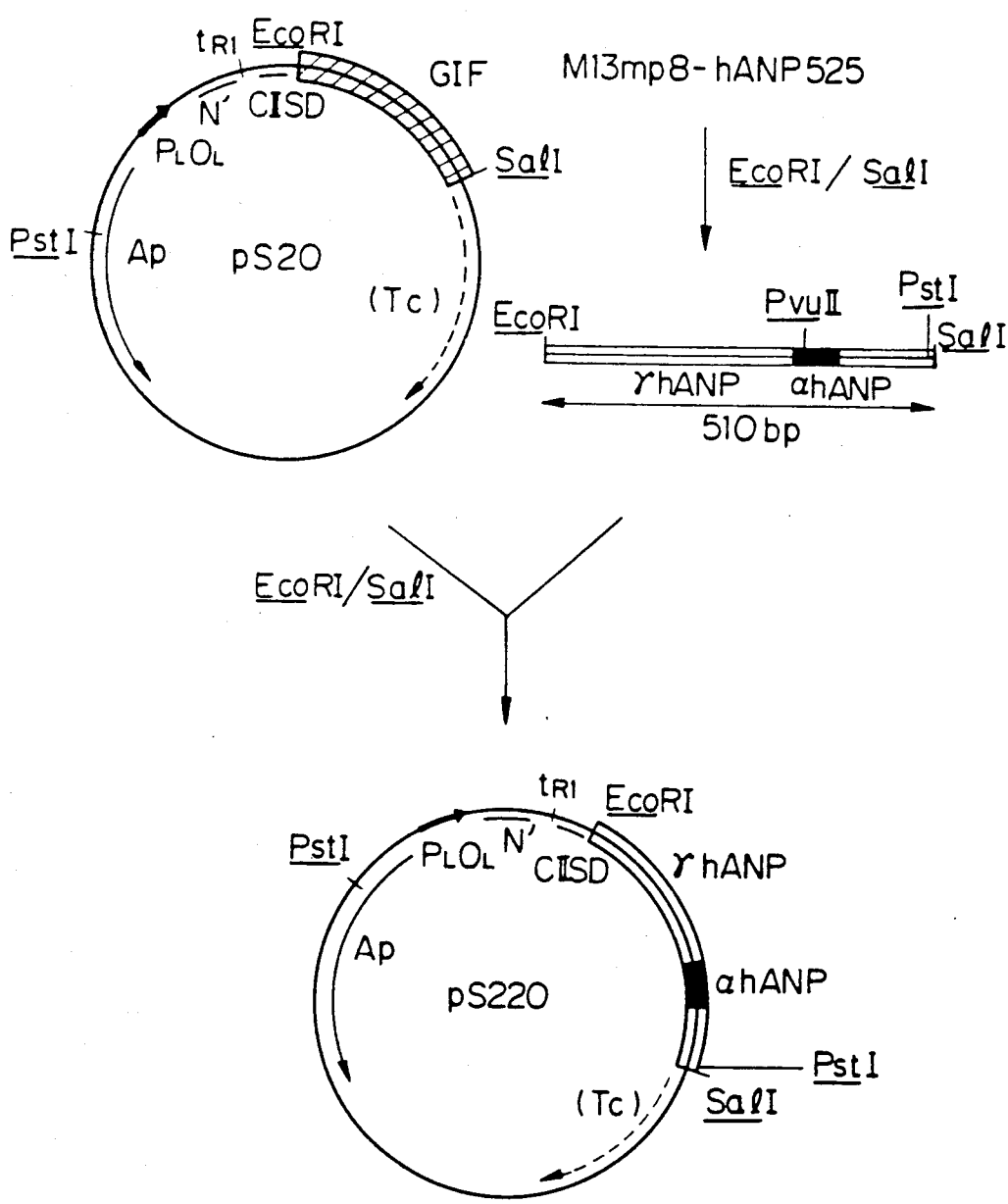
FIG. 6 represents a construction process of plasmid pS220 from a plasmid pS20 and a DNA fragment containing a base sequence coding for amino acid sequence of γ-hANP.

RNA were extracted from human atrium cordis by a method disclosed in Chirgwin (Chirgwin, J. M. et. al., Biochemistry 18, 5294-5299, 1979, and enriched for poly (A)⁻ RNA (mRNA) with an oligo (dT) cellulose column. The poly (A)⁻ RNA were used to prepare a cDNA library according to the Okayama-Berg method (Mol. Cell. Biol. 2, 161-170, 1982). The library was screened with a mixture of probes consisting of synthesized 14 meroligonucleotides labeled with $^{32}$P coding for an amino acid sequence of from 12 to 16 of α-hANP (FIG. 9), and 23 clones were selected which hybridized with the probes. Among the 23 clones, 8 clones were used to extract plasmids which were then sequenced with the mixture of probes by the dideoxy method. As a result, all of the plasmids tested contained a base sequence coding for α-hANP. Among these plasmids, two plasmids containing a longer insert DNA fragment, i.e., plasmids phANP1 and phANP82, having about 980 base pairs (pb), and about 850 pb, respectively, were selected, and the insert fragments were completely sequenced by the Maxam and Gilbert method (Meth. Enzym., 65, 499-560, 1980) and the method disclosed by Sanger et. al. (Proc. Natl. Acad. Sci. USA, 74, 5463-5467, 1977). Both fragments had a long open reading frame which starts from a translation initiation codon ATG and ends at a translation stop codon TGA. However, the fragment in the plasmid phANP82 was shorter by about 100 bp than the fragment in the plasmid phANP1. A base sequence of the fragment in the plasmid phANP82 is shown in FIG. 5. FIG. 5 also contains an amino acid sequence expected from the base sequence of the open reading frame. The expected amino acid sequence consists of 151 amino acids and includes an amino acid sequence of α-hANP already established, which sequence is shown in a box in FIG. 5.

On the other hand, a peptide having a molecular weight of about 13,000 Dalton was isolated from human atrium cordis. The peptide was sequenced, and determined to have an amino acid sequence set forth in FIG. 1 (described below in detail).

The amino acid sequence of the peptide extracted from human atrium cordis is identical with an expected amino acid sequence from the 26 position to 151 position in FIG. 5. This means that the cDNA fragment in the plasmid phANP82 contains a base sequence coding for γ-hANP. The cDNA fragment also contains an additional base sequence coding for an amino acid sequence from Met at position 1 to Ala at position 25 in FIG. 5. The amino acid sequence from 1 to 25 is believed to be a signal peptide which participates in the secretion of a peptide. As shown above and in FIG. 5, the cDNA region in the plasmid phANP82 consists of a 5' non-translation region of 90 bp, a coding region of 453 bp, and a 3' non-translation region of 300 bp. The coding region consists of a region coding for a signal sequence of from 1 to 25 in amino acid position and a region coding for γ-hANP peptide of from 26 to 151 in amino acid position. The region coding for γ-hANP peptide includes a region coding for α-hANP peptide of from 124 to 151 in amino acid position.

The above-mentioned relationship between α-hANP and γ-hANP supports the expectation that γ-hANP is a precursor of α-hANP. When α-hANP is derived from γ-hANP, an amide bond of the Pro-Arg sequence present at 122 and 123 in FIG. 5, i.e., an amide bond between Agr-Ser at 123 and 124, has to be cleaved. This possibility is strongly suggested from a phenomenon wherein gastrin releasing peptide is derived from its precursor by cleavage of an amide bond of the Pro-Arg sequence present in the precursor (Reave, J.R. et. al., J. Biol. Chem. 258, 5582-5588, 1983; and Minamino, N. et. al., Biochem. Biophys. Res. Commun. 119, 14-20, 1984). From the similarity between γ-hANP and gastrin releasing peptide in the presence of the Pro-Arg sequence, α-hANP is reasonably considered to be formed in vivo from γ-hANP by processing (perhaps by enzymic action).

2. Construction of Recombinant DNA

As DNA fragments cloned into plasmide phANP1 and phANP82 contain a base sequence coding for γ-hANP, and therefore α-hANP, both of which have natriuretic or diuretic action and hypotensive or antihypertensive action, the DNA fragments are useful for the industrial production of γ-hANP and α-hANP and other diuretic peptides having an amino acid sequence present in the γ-hANP.

For the construction of a recombinant DNA containing a base sequence coding for γ-hANP and useful for expression of the γ-hANP gene, a restriction enzyme EcoRI cleavage site and a translation initiation codon ATG were incorporated into an upstream site adjacent to the γ-hANP gene in the DNA fragment by in vitro mutation (Zoller, M. J. & Smith, M., Nucl. Acid. Res. 10, 6487, 1982). RF-DNA of M13mp8 and DNA of plasmid phANP1, were cleaved with Pst I to obtain cleaved RF-DNA of M13mp8 and a DNA fragment of about 700 bp containing the γ-hANP gene, respectively. Both DNA fragments were ligated with T4 DNA ligase, and transformed into E. coli JM103. The transformed E. coli was cultured to obtain a single strand phage containing the 700 bp fragment. The single strand phage DNA was used to form a hetero duplex with a chemically synthesized 36 mer single strand DNA. The synthesized DNA consists of a base sequence GAATTCATG coding for the above-mentioned EcoRI site and the translation initiation codon ATG and corresponding to a sequence ACC AGA GCT in FIG. 5 (shown by a dotted line), a base sequence of 12 bases identical with a sequence upstream of the dot-lined sequence, and a base sequence of 15 bases identical with a sequence downstream of the dot-lined sequence. The single strand DNA partially having the hetero duplex was converted to a double strand DNA according to a conventional method with a DNA polymerase I Klenom fragment (Zoller, J.M. & Smith, M., Nucl. Acid Res. 10, 6487, 1982). The formed double strand DNA was transformed into E. coli JM103. To select plasmid DNA containing a base sequence GAATTCATG in place of the original base sequence ACCAGAGCT, screening was carried out by culturing the transformed E. coli, obtaining DNAs, and cleaving the DNAs with EcoRI. A base sequence covering the sequence GAA TTC ATG was determined by a dideoxy chain termination method (Sanger, F. et. al., Proc. Natl. Acid. Sci. USA 74, 5463-5467, 1977), and a plasmid containing a desired sequence was selected and designated as M13mp8-hANP525.

To construct an expression plasmid, the plasmid M13mp8-hANP525 was cleaved with Eco RI and Sal I to obtain a DNA fragment of about 510 bp containing the γ-hANP gene. The Eco RI cleaves the Eco RI cleavage site incorporated by the above-mentioned in vitro mutation; and the Sal I cleaves a Sal I cleavage site originally present in M13mp8. A plasmid pS20 (FIG. 6) was cleaved with Eco RI, and Sal I, and a Eco RI - Sal I DNA fragment of about 450 bp was replaced with the above-mentioned Eco RI - Sal I fragment of about 510 bp to obtain an expression plasmid pS220 (FIG. 6). The plasmid pS20 has a λP$_L$ promotor and SD sequence of a λphage CII protein gene as a non-translation region followed by an Eco RI cleavage site, and can express foreign gene inserted at the Eco RI under the control of the λP$_L$ promotor. The plasmid pS20 has been constructed by the inventor, and deposited at the Fermentation Research Institute Agency of Industrial Science and Technology (FRI) under the Budapest Treaty on the International Recognition of the Deposit of Microorganisms for the Purposes of Patent (Budapest Treaty) as FERM BP-535 on May 30, 1984.

Figure 7:
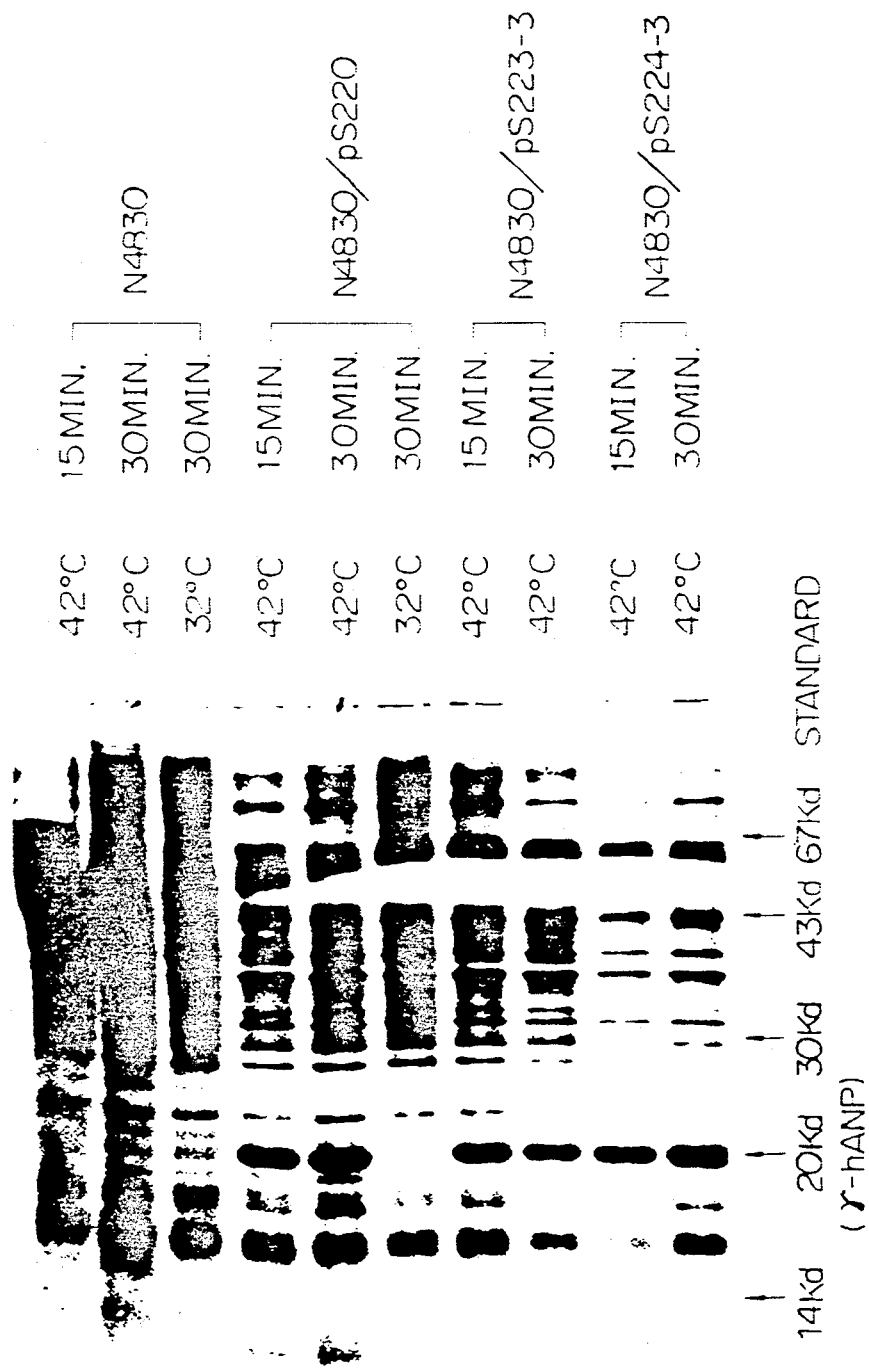
FIG. 7 represents a result of electrophoresis showing expression of a γ-hANP gene.

The plasmid pS220 was transformed into E. coli N4830, and the transformed strain was cultured in a minimum medium M9 supplemented with 50 µg/ml ampicillin and 19 natural amino acids except for L-methionine at a temperature of 32° C. When the E. coli was grown to OD$_{660}$=0.4, the temperature was shifted from 32° C. to 42° C., and $^{35}$S-methionine was added to the culture to pulse-label the newly synthesized protein for two minutes. Culturing was continued for an additional 15 minutes or 30 minutes, and terminated by the addition of trichloroacetic acid. A control culture was prepared with E. coli N4830 not containing plasmid pS220. Proteins were extracted and analyzed with SDS-polyacrylamido gel electrophoresis (SDS-PAGE) to determine the composition of the proteins. The culture of E. coli containing plasmid pS220 provided a band of about 20Kd which was not found in the control culture (FIG. 7). This means that the plasmid pS220 expressed a new protein with about 20Kd.

Figure 8:
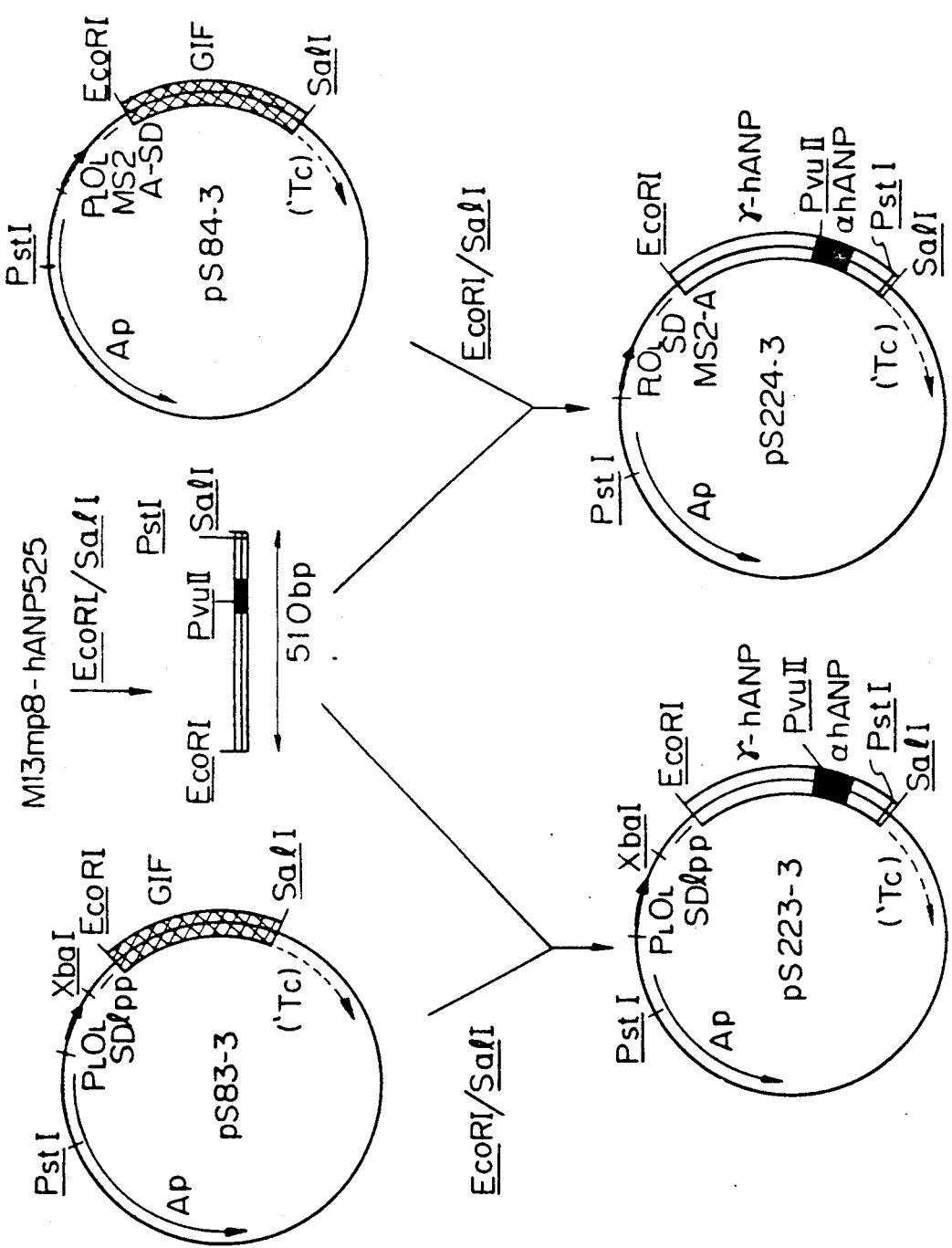
FIG. 8 represents a construction process of plasmid pS223-3 from plasmid pS83-3 and a DNA fragment containing a base sequence coding for amino acid sequence of γ-hANP, and a construction process of plasmid pS224-3 from plasmid pS84-3 and the same DNA fragment.

Moreover, plasmid pS223-3 and pS224-3 were constructed. The plasmid pS223-3 was constructed from plasmid pS83-3 and an Eco RI - Sal I DNA fragment of about 510 bp containing the γ-hANP gene from the M13mp8-hANP525. The plasmid pS223-3 contains an SD sequence of the lpp gene in place of the region flanked by the λP$_L$ promotor and a translation initiation codon ATG in plasmid pS220 (FIG. 8). The plasmid pS224-3 was constructed from plasmid pS84-3 and the above-mentioned 510 bp DNA fragment. The plasmid pS224-3 contains an SD sequence of the MS2 phage A protein in place of the region flanked by the λP$_L$ promoter and the ATC (FIG. 8). Both E. coli transformed with pS223-3 and E. coli transformed with pS224-3 produced the same proteins as those produced by E. coli transformed with pS220.

While the molecular weight (about 20Kd) shown on the SDS-PAGE is higher than a theoretical molecular weight of γ-hANP (13,679 Dalton), the protein showing about 20Kd was determined to be γ-hANP because γ-hANP prepared from human atrium cordis migrates to a site corresponding to 20Kd on the SDS-PAGE, and because the SDS-PAGE often shows a molecular weight higher than a theoretical molecular weight for other proteins.

This conclusion was confirmed as follows: a chemically synthesized linker,

GATTCATTCATTCAGCT wherein the underlined portions are translation termination codons, and each of the codons corresponds to any one of three kinds of reading frames, was incorporated into a site downstream of the γ-hANP gene in a expression plasmid. The E. coli transformed with the plasmid having the three additional termination codons again produced a protein having a 20Kd molecular weight on the SDS-PAGE. This result negates the possibility that the translation termination codon TGA present at the next position to the 151st codon TAC in FIG. 5 was translated.

Thus, it was confirmed that γ-hANP, which is a precursor of α-hANP, can be produced by a microorganism using a recombinant gene according to the present invention.

Wherein, although construction of plasmids containing a base sequence coding for an amino acid sequence from 26 to 151 in FIG. 5 (γ-hANP) as a coding region are represented, other plasmids containing a base sequence coding for an amino acid sequence from 1 to 151 in FIG. 5 (signal sequence and γ-hANP), and plasmids containing a base sequence coding for an amino acid sequence from 124 to 151 (α-hANP) or any other amino acid sequence as a coding region can be constructed by the same procedure. Moreover, although cDNA corresponding to mRNA prepared from human atrium cordis was represented as a γ-hANP gene, gene coding for γ-hANP can be chemically synthesized. Moreover, although the γP$_L$ promotor was represented as a promotor region in expression plasmids, other promotors can be used. For example, to express the gene in E. coli, a promotor region of tryptophan gene (trp), lactose gene (ac), lipoprotein gene (pp), alkaline phosphatase genes (PHOA, PHOS, etc.) or outer membrance protein gene (omp), or a hybrid promotor of tryptophan and lactose promotors (tac promotor) can be used. To express the gene in yeast, a promotor region of alcohol dehydrogenase gene (ACH), glyceraldehyde dehydrogenase gene (GAP-DH), phosphoglycerokinase gene (RGK), or repressible acid phosphatose gene can be used. Moreover, to express the gene in animal cells, or a promotor region of SV40, an early or late gene can be used.

3. Preparation of γ-hANP from Human Atrium Cordis γ-hANP can be produced by the extraction of the γ-hANP from human atrium.

In the process, human atrium is homogenized in an acidic aqueous solution such as a phosphate buffer solution, or an acetic acid solution containing hydrochloric acid. Subsequently, γ-hANP is purified according to a conventional method suitable for the purification of peptide, such as centrifugation, isoelectric point precipitation, solvent extraction, ultrafiltration, gel filtration, adsorption chromatography or high performance liquid chromatography (HPLC), or a combination of such methods. In the above-mentioned methods, chicken rectum relaxation activity is conveniently used to select fractions containing γ-hANP, because γ-hANP has this activity In the chromatography methods, the α-hANP containing fractions can be also selected by molecular weight (about 14,000).

20 4 Structure and Physico-chemical Properties of γ-hANP

1) Structure:
The γ-hANP has the structure set forth in FIG. 1.
2) Molecular weight: about 13,000 as determined by gel-filtration and about 20,000 as determined by SDS-PAGE (13679 as calculated).
3) UV spectrum: Max =276 mm.
4) Color reactions: Ehrlich's reaction, negative; Sakaguchi's reaction, positive; Pauly's reaction, positive.
5) Distinction of basic, acidic or neutral property: basic.
6) Solubility in solvents: soluble in water, methanol, and acetic acid; insoluble in ethyl acetate, butyl acetate, ethyl ether, hexane, petroleum ether, benzene, and chloroform.
7) Amino acid composition by amino acid analysis:

| Amino acid | Mol. ratio | |
|---|---|---|
| | found | calculated |
| Asx | 13.69 | 14 |
| Ala | 11.98 | 11 |
| Arg | 10.24 | 10 |
| Ile | 1.45 | 1 |
| Gly | 11.61 | 11 |
| Glx | 13.22 | 12 |
| (Cys)₂ | 0.16 | 1 |
| Ser | 12.37 | 13 |
| Tyr | 2.01 | 2 |
| Phe | 3.48 | 3 |
| Met | 3.61 | 4 |
| Leu | 17.22 | 16 |
| Val | 5.98 | 6 |
| Thr | 2.68 | 2 |
| His | 1.43 | 1 |
| Lys | 5.14 | 4 |

8) Formation of salts: the γ-hANP is a basic compound as described in item 5), and can form acid addition salts with an inorganic acid such as hydrochloric acid, sulfuric acid, phosphoric acid, or an organic acid such as formic acid, acetic acid, propionic acid, succinic acid, and citric acid.

5. Physiological Properties of γ-hANP

The γ-hANP according to the present invention has notable diuretic, and hypotensive or antihypertensive actions.

Test method

Male rats weighing 300 to 400 grams were anesthetized by intraperitoneal administration of pentobarbital at a dosage of 60 mg/kg, and used for tests on the γ-hANP according to the method described in *Life Sciences*, Vol. 28, pp89-94, 1981, A.J. deBold, et.al.

To keep the respiratory tract open, a tracheal cannula (PE-240 Clay-Adams) was inserted into the trachea. An arterial cannula (PE-50) was inserted into a femoral artery for measurement of the blood pressure, and a venous cannula was inserted into a femoral vein for the administration of Ringer's solution. 1.2 ml of Ringer's solution was injected for ten minutes, and subsequently, was constantly infused at a flow rate of 1.2 ml/hour.

A bladder cannula made of silastic tube with a inner diameter of 0.02 inches and an outer diameter of 0.037 inches was inserted into the bladder, and via the cannula, a urine sample was collected into a test tube. The collection of urine was carried out for 30 minutes before administration of the test compound, and 5, 10, 20, 30, and 60 minutes after the administration.

1 nmole of the test compound γ-hANP was dissolved in 50 μl of sterilized physiological saline with 5 μg of bacitracin, and the solution was injected into the jugular vein.

Figure 11:
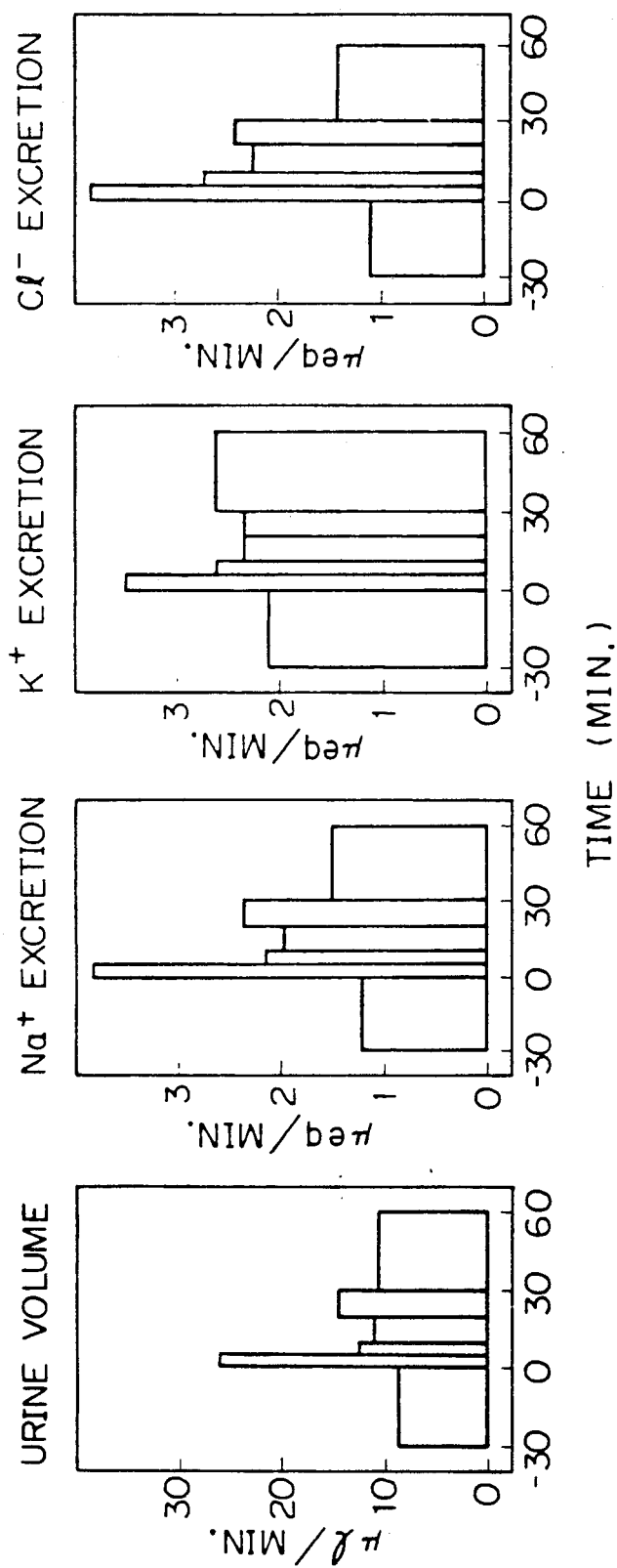
FIG. 11 represents graphs showing diuretic action of γ-hANP.

As shown in FIG. 11, γ-hANP shows a notable diuretic action. Moreover, as shown in FIG. 12, after 1 mole of γ-hANP is administered to a rat, the blood pressure is gradually lowered by about 20 mmHg for about 1 hour, revealing that γ-hANP has a hypotensive action or antihypertensive action, and may be useful as a hypotensor.

6. Use of γ-hANP as a pharmaceutical product

Repeated administration of γ-hANP does not stimulate production of antibodies, and does not cause anaphylaxis shock. γ-hANP consisting of L-amino acids is gradually hydrolyzed in a body providing the L-amino acids, and therefore shows little toxicity.

Due to the higher diruetic, and blood pressurelowering or antihypertensive actions, and the lower toxicity, γ-hANP on acid addition salts thereof is useful as an active ingredient for pharmaceutical compositions such as a direutic and a hypotensor. γ-hANP is administered at 1 μg/kg to 10 mg/kg, preferably 10 μg/kg to 1 mg/kg.

γ-hANP can be administered in the same manner as conventional peptide type pharmaceuticals. Namely, γ-hANP is preferably adminstered parenterally, for example, intravenously, intramuscularly, intraperitoneally, or subcutaneously. γ-hANP, when administered orally, may be proteolytically hydrolyzed. Therefore, oral application is not usually effective. However, γ-hANP can be administered orally as a formulation wherein γ-hANp is not easily hydrolyzed in a digestive tract, such as liposome-microcapsules. γ-hANP may be also adminstered in suppositories, sublingual tablets, or intranasal spray.

The parenterally administered pharmaceutical composition is an aqueous solution containing about 0.000005 to 5%, preferably 0.00005 to 0.5% of γ-hANP, which may contain, in addition to γ-hANP as an active ingredient, for example, buffers such as phosphate, acetate, etc., osmotic pressure-adjusting agents such as sodium chloride, sucrose, and sorbitol, etc., antioxidative or antioxygenic agents, such as ascorbic acid or tochopherol, and preservatives, such as antibiotics. The parenterally administered composition also may be a solution readily usable or in a lyophilized form which is dissolved in sterile water before administration.

EXAMPLES

The present invention will now be further illustrated by, but is by no means limited to, the following examples.

EXAMPLE 1

1) Preparation of cDNA library, and isolation and identification of α-hANP gene (1-a) Preparation of cDNA library From two human atrium cordis obtained from an 82 years old female and 61 year old male, 1 mg of RNA was extracted with 4M guanidium thiocyanate according to a method of Chirgwin et al. (Chirgwin, J.M. et. al., Biochemistry 18, 5294-5299, 1979). The RNA was then subjected to an oligo (dT) cellulose column using 10 mM Tris-HCl buffer, pH 7.2, containing 0.5M LiCl, 10 mM EDTA and 0.5% SDS as a binding buffer, and 75 μg of poly (A) -RNA (mRNA) was isolated (Nakazato, H. & Edmonds, D.S., Meth. Enzym. 29, 431-443, 1974). 15 μg of the poly (A) RNA and 4.2 μg of vector primer DNA were used to prepare a cDNA library (plasmids) according to the Okayama-Berg method (Mol. Cell Biol. 2, 161-170, 198), and the cDNA library was used to transform *E. coli* WA802. The transformants were screened on an LB-agar medium supplemented with 40 γ/ml of ampicillin, and about 40,000 colonies of ampicillin resistant transformants were obtained per microgram of starting mRNA.

(1-b) Isolation of α-hAMP clone

About 40,000 colonies were replicated on a nitrocellulose filter, and the filter was incubated on an LB agar plate supplemented with 40 γ/ml of ampicillin at 37° C. for 6 hours. The filter was transferred onto an LB agar plate supplemented with 180 γ/ml of chloramphenicol incubated at 37° C. over night. The colonies on the filter were lyseated with 0.5 N NaOH, and neutralized to pH 7.0, and the filter was soaked in 0.5 M Tris -HCl buffer, pH 7.0, containing 1.5 N NaCl, and in 3 ╱ SCC (0.15 M NaCl, 0.05 M sodium citrate) for 5 minutes respectively. Finally, cell debris on the filter was removed with a paper towel, and the filter was air-dried and then baked at 80° C. for 2 hours. The filters were then subjected to hybridization with a mixture of probes I and II (FIG. 9) consisting of chemically synthesized 14-mer oligonucleotides labeled with $^{32}$p at their 5'-end (Grunstein, M. & Hogness, D.S., Proc. Natl. Acad. Sci. USA, 72, 3961-3965, 1975). The 14-mer oligonucleotides used as a probe are possibly complemental with mRNA coding for an amino acid sequence Met-Asp-Arg-Ile-Gly (an amino acid sequence from 135 to 139 in FIG. 5), and have been labelled with $^{32}$p at their 5'-end using 32p Y-ATP and T4 kinase and have a specific activity of 1 to $3 \times 10^6$ cpm/p mole. The hybridization was carried out in 3╱ SCC containing 1× Denhardts (0.2% BSA, Armour Pharmaceutical Company; 0.2% Ficol, Sigma; and 0.2% polyvinyl pyrrolidone, Wako Jyunyaku), 0.1% SDS and 50 μg/ml salmon testis DNA, at 38° C. for 16 hours. The filter was then washed with 3×SCC containing 0.1% SDS, air-dried, and placed in contact with an X-ray film. As a result, 85 positive clones were observed on the film. The 85 positive clones were then subjected to the colony hybridization using the same procedure as described above, except that the probe I and probe II were separately used at 40° C. and 38° C. for each probe. As a result, 23 clones were obtained which hybridize with the probe II but do not hybridize with the probe I. Among these 23 clones 8 clones were used to isolate plasmid DNA according to a conventional method. The isolated plasmid DNAs were sequenced using the probe II as the primer according to a dideoxy chain termination method (Sanger F. et al. Proc. Natl. Acad. Sci. USA, 74, 4563-5467, 1977). As a result, all of the plasmids contained a base sequence corresponding to a part of an amino acid sequence of α-hANP and, consequently, the above-mentioned 8 clones were confirmed to have a plasmid containing cDNA of α-hANP Among the 8 plasmids, 2 plasmids having a longer insert containing cDNA of γ-hANP were selected, and designated as phANP 1 and phANP82. The inserts of plasmids phANP1 and phANP82 were sequenced. As a result, the plasmids phANP1 and phANP82 contained an insert of about 950bP and an insert of about 850bp, respectively.

Figure 10:
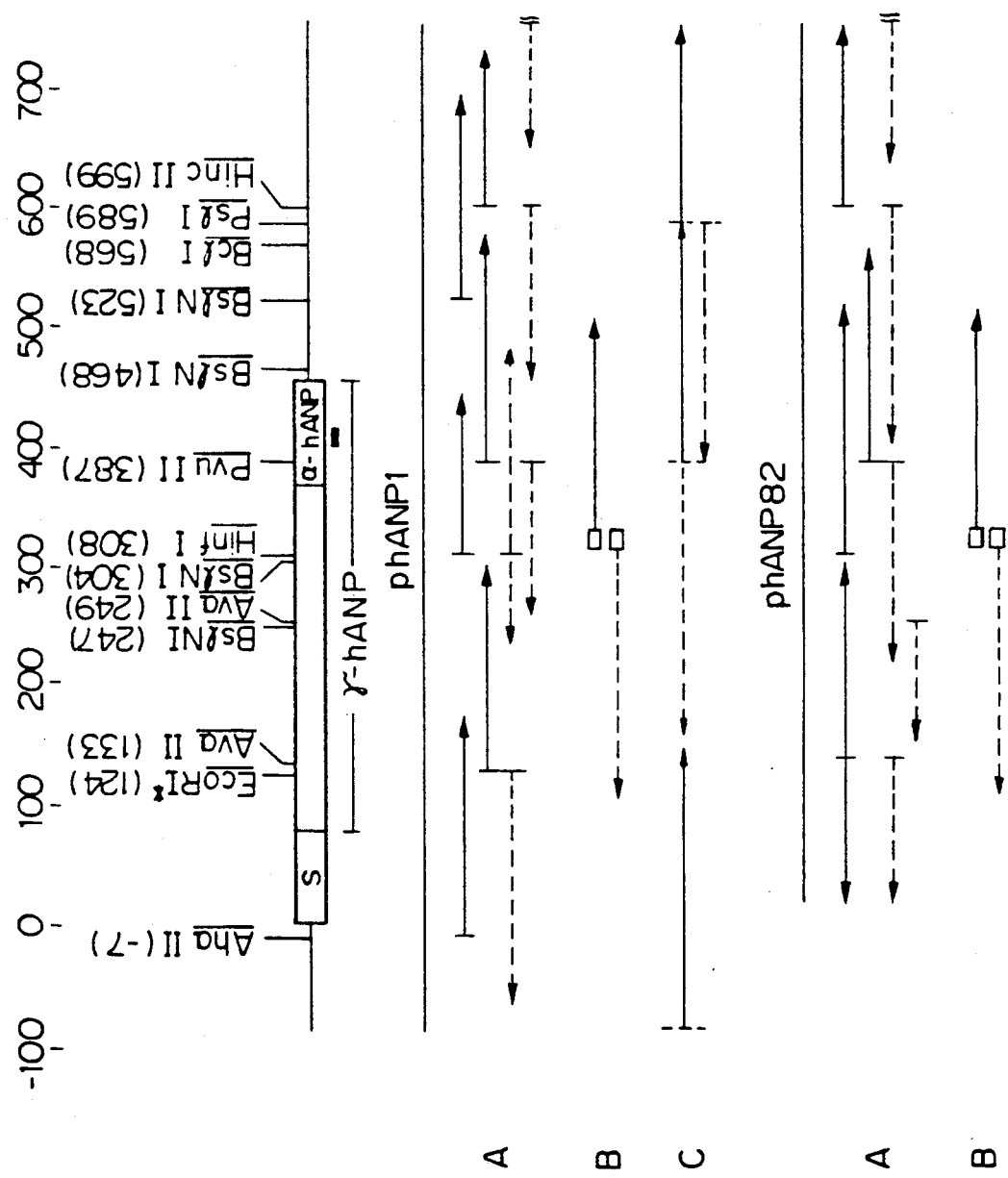
FIG. 10 represents a strategy used for sequencing DNAs of plasmid phANP1 and phANP82.

Restriction enzyme sites of the insert DNA region and a strategy for sequencing the insert DNA region are set forth in FIG. 10. In FIG. 10, the direction for sequencing is shown by arrows, wherein solid lines show an upper strand and dotted lines show a lower strand. The sequencing was carried out according to the Maxam-Gilbert method (Meth. Enzym., 65, 499-560, 1980) and Sanger method (Proc. Natl. Acad. Sci. USA, 74, 5463-5467, 1977). A shows the sequencing according to the Maxam-Gilbert method; B shows the sequencing according to the Sanger method; and C shows the sequencing wherein each plasmid phANP1 and phANP82 was cleaved with PstI and PvuII to obtain 3 fragments, and then each fragment was inserted into plasmid pUC8 (Vieira, J. & Messing, J., Gene 19, 259-268, 1982) and sequenced according to the Sanger method.

As a result of the above-mentioned sequencing, it was confirmed that the base sequences of inserts present in the plasmids phANP1 and phANP82 were identical except that the insert in the plasmid phANP1 has an additional base sequence of about 100bp as the 5' non-translation region. FIG. 5 shows the base sequence of the insert in phANP82 and an amino acid sequence corresponding to an open reading frame in the insert. The insert DNA contains the reading frame starting from ATG and ending at a translation termination codon TGA, and the reading frame includes a base sequence coding for 60 -hANP at the 3' terminal side (C terminal side in the amino acid sequence). On the basis of an amino acid sequence of γ-hANP purified from human atrium cordis and identified, which has an N terminal sequence H-Asn-Pro-Met-Tyr-Asn- . . . and C terminal sequence . . . -Asn-Ser-Phe-Arg-Tyr-OH as set forth in FIG. 1, the reading frame was confirmed to contain a coding region of from codon AAT of Asn at 26 to codon ATC of Tyr at 151 in FIG. 5.

In FIG. 5, an amino acid sequence of from Met at 1 to Ala at 25 is considered from its characteristic sequence to be a signal sequence participating in the secretion of peptide. The base sequence in FIG. 5 also contains a sequence AATAAA shown by a solid underlining, which sequence is known to precede polyadenylation site in many eukaryotic mRNA.

2) Construction of γ-hANP gene expression vector (2-a) Insertion of γ-hANP gene into M13 DNA 0.44 μg of M13mP8 RF-DNA was cleaved with 16 units of PstI in 20 μ of Medium-Salt Buffer (10 mM Tris-HCl buffer, pH 7.5, containing 50 mM NaCl, 10 mM MgCl, 1 mM DTT) at 37° C. for 1 hour. The mixture was then heated at 65° C. for 10 minutes to stop the enzyme reaction. On the other hand, 20 μg of plasmid phANP1 DNA was cleaved with 160 units of PstI in 100 μ of the Medium Salt Buffer at 37° C. for 1 hour, and the reaction mixture was subjected to 1 % agarose gel electrophoresis. A part of the gel containing a DNA fragment corresponding to about 700bp was cut to obtain an agarose piece, and the DNA fragment was extracted by the electro-elution method and purified.

66 ng of the DNA fragment from M13mp8 RF-DNA and 1 μg of the 700 bp DNA fragment were ligated using 5.6 units of T4 DNA ligase (Takara Shuzo, Japan) in 20 μl of ligation buffer (20 mM Tris-HCl buffer, pH 7.6, containing 10 mM MgCl$_2$, mM ATP, 5 mM DTT) at 14° C. for 16 hours. E. coli JM103 cells were treated with CaC$_2$ according to a conventional method to obtain a suspension of the E. coli cells in 50 mM CaCl$_2$, and the ligation mixture prepared as above (20 μ) was added to the E. coli suspension to transform the E. coli.

The transformant clones were screened as follows. The suspension containing transformant E.coli cells was diluted in YT soft agar medium containing X-Gal and IPTG (prepared by adding 10 μl of 10 mM IPTG, 50 μ of 2% X-gal and 0.2 of E. coli JM103 suspension grown in a logarithmic growth phase into 3 ml of solution containing 0.6% agar, 0.8% Bacto trypton, 0.5% yeast extract and 0.5% NaCl). 0.3 ml of the diluted suspension was spread on YT agar medium (1.5% agar, 0.8% Bacto trypton, 0.5% yeast extract and 0.5% NaCl), and incubated at 37° C for 16 hours to form plaques. Among the plaques, 10 plaques were selected, and inoculated into 2 · YT liquid medium (1.6% Bacto trypton, 1% yeast extract and 1.0% NaCl) and cultured at 37° C. for 8 hours. 1 ml of the cultured medium was centrifuged at 10,000 rpm for 10 minutes to recover a supernatant containing phage. The phage DNA (single strand (DNA) was isolated and purified as follows.

To 800 μl of the phase liquid, 200 μl of 20% polyethylene glycol (PEG 6000) containing 2.5N NaCl was added, and the mixture was allowed to stand at room temperature for 20 minutes and centrifuged at 10,000 rpm for 5 minutes to precipitate the phage. The precipitated phage was dissolved in 100 μl of TE buffer (10 mM Tris-HCl, pH 8.0, 1 mM EDTA), and to the solution 50 μl of phenol saturated with water was added, the mixture was vigorously stirred for 5 minutes, and centrifuged at 10,000 rpm for 5 minutes. After sampling 80 μl of the aqueous phase, to the aqueous phase 3 μof 3M sodium acetate, pH 8.0, and 200 μl of ethanol was added, and the mixture was cooled at −70° C. for 10 minutes, and then centrifuged at 10,000 rpm for 10 minutes to precipitate DNA. The precipitated DNA was washed once with ethanol, and dissolved in 50 μl of the above-mentioned TE buffer. A part of a base sequence of each phage DNA was sequenced according to the dideoxy chain termination method (Methods in Enzymology, 65, 560–580, 1980, Academic Press, N.Y.), and among 10 clones, 2 clones containing a lower strand (DNA fragment having a base sequence complementary to mRNA) were selected. The phage DNA thus obtained were used as a template for in vitro mutation.

(2-a) Incorporation of EcoRI cleavage site and translation initiation codon by in-vitro mutation To 5 μl of the single strand phage DNA solution described above, 1 μl of 0.2M Tris-HCl buffer, pH 7.5, containing 0.1 M MgCl$_2$ and 0.5M NaCl, and 2 μl of water, were added 2 μl of solution containing 10 pmole of 36-mer chemically synthesized DNA fragment (5'-CTCCTAGGTCAGGAATTCATGAATCCCATG-TACAAT-3') phos-, phorylated at the 5' end to form 10 μl of a mixture. The mixture was heated at 65° C. for 5 minutes, and allowed to stand for 10 minutes at room temperature.

To the mixture, 1 μl of 0.2 M Tris-HCl buffer (pH7.5) containing 0.1 M MgCl, 2 μof 0.1 M DTT, 1 μl of 10 mM ATP, 2 μl each of 10 mM dATP, dDTP, dCTP and dTTP, 2 μl of water, 5 units of DNA polymerase I Klenow fragment (Boehringger Manheim) and 2.8 units of T4 DNA ligase (Takara Shuzo) were added, and the mixture was incubated at 15° C. for 16 hours. 20 μl of the reaction mixture was used to transform E. coli JM103.

As described above for the preparation of phage DNA, plagues were formed on a YT soft agar medium, and 48 clones were selected. The clones were inoculated to 2×YT medium, and cultured at 37° C. for 8 hours. 1 ml of the cultured medium was centrifuged at 10,000 rpm for 10 minutes to recover the supernatant as phage solution. On the other hand, RF-DNA was extracted and isolated from the precipitated cells according to the alkaline extraction method (Birnboim, H.C. & Doly, J., Nucl. Acid. Res., 7, 1513–1523, 1979). The RF-DNA was then cleaved with 4.2 units of EcoRI (Takara Shuzo) in EcoRI buffer (100 mM Tris-HCl, pH 7.5, 50 mM NaCl, 5 mM MgCl$_2$) at 37° C. for 1 hour. The reaction mixture was subjected to 2% agarose gel electrophoresis, and a clone providing a DNA fragment of about 530bp was selected. The clone was designated as M13mp8-hANP525.

To 400 ml of 2×YT liquid medium, 0.4 ml of culture of E. coli JM103 infected with the above-mentioned phage clone and 4 ml of a not-infected culture of E. coli JM103 were inoculated. The medium was then incubated at 37° C. for 12 hours. The cultured medium was centrifuged to obtain an infected cell precipitation and a supernatant phage solution. From the infected cells, RF-DNA was obtained by a density-gradient centrifugation method using cesium chloride and ethidium bromide according to a conventional method. On the other hand, from the supernatant phage solution phage DNA was obtained, and the phage DNA was sequenced according to the dideoxy chain termination method. As a result, it was confirmed that a translation initiation codon ATG and Eco RI cleavage recognition site GAATTC, i.e., a base sequence GAATTC ATG, were inserted immediately upstream of the γ-hANP gene.

(2-c) Construction of expression vector for γ-hANP gene FIG. 6, FIG. 8)

An expression plasmid pS220 was constructed from plasmid pS20 and M13mp8-hANP525. The starting plasmid pS20 was constructed by the inventors, and E. coli N4380/pS20 containing the plasmid pS20 was designated as SBM271, and deposited as FERM BP-535 as described above. The plasmid pS20 contains λ- phage P$_L$ promoter, and can express a foreign gene inserted to a site downstream of the promoter under the control of the promoter.

The plasmid pS20 was constructed as follows. Bacteriophage λ-C1857 DNA was cleaved with BamHI and Hind III to obtain a 2.4 kb DNA fragment containing the γP$_L$ promoter. The DNA fragment was inserted into a region of Hind III-Bam HI in pBR322 to obtain a plasmid which is substantially the same as the plasmid pKO 30 described in Nature 292, 128,1981. To the Hpa I cleavage site of the plasmid thus obtained, 1.3 Kb Hae III DNA fragment containing NutR, tR$_1$, CII and a part of O protein derived from bacteriophage λcy3048 (from Dr. Hiroyuki Shimatake, Medical Department, Toho University) was inserted to obtain plasmid (pS9), wherein CII is present in the direction the same as the transcription direction of λP$_L$. The plasmid (pS9) was cleaved with Bgl II and Rsa I to obtain a 0.65 Kb DNA fragment containing PL promotor, DNA sequence of protein N' which is a part of an N protein lacking a C terminal, and the Shine-Dalgarno sequence (SD) of a CII gene. The Rsa I and of the 0.65 Kb DNA fragment was added with the Eco RI linker:

—CGGAATTCCG—

—GCCTTAAGGC—

(New England Biolabos, Inc.), and then the Bgl II end of the same DNA fragment was converted to a blunt end with T4 DNA polymerase. The DNA fragment thus obtained was ligated with a DNA fragment prepared by Eco RI cleavage of plasmid pBR322 and conversion of the pBR322 ends to blunt ends to form a plasmid (pS13). In the plasmid (pS13), the P$_L$ promotor is oriented in the direction the same as the transcription direction of the tetracycline resistant gene (Tc$^r$) derived from pBR322. The plasmid (pS13) was cleaved with Eco RI and Sal I, and a large fragment was isolated. The large fragment was then ligated with a DNA fragment containing a foreign gene, i.e., human γ-interferon gene GIF, which fragment was prepared by cleavage of plasmid pGIF4 with Eco RI and Sal I. The plasmid pGIF4 was disclosed in Japanese Unexamined Patent Publication No. 58-201995 (U.S. Ser. No. 496176), and E. coli containing the plasmid was designated as SBMG 105 and deposited at the FRA under the Budapest Treaty on the International Recognition of the Deposit of Microorganisms for the Purpose of Patent Procedure as FERM BP-282 on May 6, 1982.

Starting with the plasmid pS20 and M13mp8-hANP525, the Y-hANP expression vector pS220 was constructed as follows. To 70 μl of Eco RI reaction buffer (100 mM Tris-Hcl, pH 7.3, 50 mM NaCl, 5 mM MgCl$_2$) containing 8 μg of M13mp8-hANP525 DNA, 15 units of Eco RI and 15 units of Sal I were added, the reaction mixture was incubated at 37° C. for 1 hour, and then subjected to the 1.0% agar gel electrophoresis. About 510 bp Eco RI - Sal I DNA fraction containing γ-hANP gene was extracted from the agar gel and purified by the electroelution method described above. On the other hand, to 50 μl of Eco RI reaction buffer containing 2 μg of Plasmid pS20 DNA, 10 units of Eco RI and 10 units of Sal I were added, and the reaction mixture was incubated at 37° C. for 1 hour, and then subjected to 1.0% agar gel electrophoresis. According to the above-mentioned electroelution, about 4.3 Kb Eco RI - Sal I DNA fragment containing the λP$_L$ promotor and the SD sequence of the CII gene was obtained. 3 μl of an aqueous solution of the Eco RI - Sal I DNA fragment containing γ-hANP gene and 10 μl of an aqueous solution of the Eco RI - Sal I DNA fragment derived from plasmid pS20 were mixed. To the mixture, 3 μl of ligation buffer with 10 times the concentration described in section (2-a), 3 μl of 100 mM DTT, 3 μl of 1 mM ATP aqueous solution, 6 μl of distillated water, and 2 units of T4 DNA ligase were added, and the mixture was incubated at 16° C. overnight to obtain a ligation mixture. The ligation mixture was used to transform E. coli N4830 (from Pharmacia P-L Biochemicals) as follows. The E. coli cells were treated according to a conventional procedure to obtain competent cells. To 300 μl of the treated E. coli cell suspension containing 50 mM CaCl$_2$, 10 μl of the ligation mixture obtained as above was added, and the resulting mixture was allowed to stand for 1 hour in ice. 2.5 μl of L-broth was added to the mixture, which was then incubated at 32° C. for 1.5 hours. The resulting mixture was plated on a nutrient agar medium containing 50 μg/ml of ampicillin to select ampicillin resistant colonies which are transformants. The transformants formants were treated according to a conventional procedure to isolate plasmid DNAs. The plasmids were screened by analysis using restriction enzymes. A plasmid having the γ-hANP gene downstream of the ΞP$_L$ promoter was selected, and designated as pS220. The transformant containing the plasmid pS220 was designed as E. Coli N4380/pS220, and was used in the test for γ-hANP production as described below in detail.

In addition to the γ-hANP gene expression vector pS220, other γ-hANP gene expression vectors were concentrated as follows. Plasmid pS20 (FIG. 6) was cleaved with Eco RI, and hydrolyzed with an exonuclease Bal 31 to form DNA fragments having various lengths. The DNA fragments were ligated with Xba I linker (from New England Biolabos Inc.; dCTCTAGAG) to obtain plasmid pS20X. The plasmid pS20X was cleaved with Xba I and Sal I to delete any Xba I - Sal I short fragments. On the other hand, plasmid pIN4GIF54 was cleaved with Xba I and Sal I to obtain a short Xba I - Sal I fragment containing human γ-interferon gene, which short fragment was then inserted to the above-mentioned cleaved pS20X in place of the deleted Xba I - Sal I fragment to form plasmids. Among the plasmids thus formed, a plasmid which can effectively express the human γ-interferon gene when transformed into E. coli was designated as pS83-3. The above-mentioned plasmid pIN4GIF54 and a method for measuring an amount of γ-interferon were disclosed in Japanese Unexamined Patent Publication No. 60-24187 (U.S. Pat. Ser. NO. 632204). As shown in FIG. 8, plasmid sP83-3 was cleaved with Eco RI and Sal I to delete the Eco RI - Sal I short fragment consisting of the human γ-interferon gene (GIF). The plasmid M13mp8-hANP525 was cleaved with Eco RI and Sal I to obtain an about 510 bp Eco Ri - Sal I fragment containing γ-hANP gene, which fragment was then inserted to the cleaved pS83-3 in place of the deleted Eco RI - Sal I fragment consisting of GIF to form plasmid pS223-3. The plasmid pS223-3 contains an λP$_L$ promotor region, SD sequence of E. coli lpp gene, and γ-hANP gene, in this order. E. coli N4380 transformed with the plasmid pS223-3 was designated as E. coli N4380/pS223-3, and used in the test for Y-hANP production as described below in detail.

Another γ-hANP gene expression vector pS224-3 was constructed as follows. The plasmid pS83-3 was cleaved with Xba I and Eco RI to delete the SD sequence of the lpp gene, and in place of the deleted SD sequence of the lpp gene, a chemically synthesized DNA fragment AGGAGGT with Xba I and Eco RI cohesive ends, which is the SD sequence of the bacteriophage MS2A protein gene, was inserted into the cleaved pS83-3 to form plasmid pS84-3. As shown in FIG. 8, the plasmid pS84-3 DNA was cleaved with Eco RI and Sal I to delete the Eco RI - Sal I short fragment consisting of GIF. The plasmid M13mp8-hANP525 DNA was cleaved with Eco RI and Sal I to obtain an about 510bp Eco RI - Sal I fragment containing the γ-hANP gene, which fragment was then inserted into the cleaved pS84-3 DNA in place of the deleted Eco RI - Sal I fragment consisting of GIF to obain plasmid pS224-3. The plasmid pS224-3 thus obtained contained a λp$_L$ promotor region, SD sequence of MS2A, and γ-hANP gene, in this order. E. coli N4380 transformed with the plasmid pS224-3 as designated as E. coli N4380/pS224-3, and tested for the production of γ-hANP.

3) Production of γ-hANP by transformant

Three transformants, i.e., E. coli N4830/pS220, N4830/pS223-3 and N4830/pS224-3, and a control strain E. coli N4830 containing no plasmid were compared. Each of these four strains was cultured in an M9 minimum medium supplemented with 50 μg/ml of ampicillin and 19 natural amino acids except for L-methionine at 32° C. until the optical density at 660 nm (OD 660) of the culture reached 0.4. At this point each culture was divided into two cultures. One of the divided cultures was cultured at the same temperature, i.e., 32° C.; and the other was cultured at 42° C. At 15 minutes and 30 minutes after the division of the culture, 0.3 ml of culture was obtained from each culture, and to the culture (0.3 ml), 2 μCi of $^{35}$S-methionine with 800 Ci/m mole of specific activity (New England Nuclea) was added. Culturing was continued for 2 minutes and then trichloroacetic acid was added to the concentration of 10% to each culture, which was then cooled to 0° C. The mixture was then centrifuged for 10 minutes, and the precipitate was washed once with ethanol and subjected to the 15% SDS polyacrylamide gel electrophoresis to separate proteins. The gel was dried and subjected to a radioautography to detect bands of proteins labeled with $^{35}$S-methionine.

As shown in FIG. 7, for cultures at 42° C. of three transformants, i.e., N4830/pS220, N4830/pS223-3, and N4830/pS224-3, a protein band corresponding to a molecular weight of 20Kd was found. The 20Kd band was not found for a culture at 32° C. of the three transformants, and a culture at 32° C. and 42° C. of the control strain. This means that a protein corresponding to the 20Kd band was produced by expression of the γ-hANP gene under the γP$_L$ promotor. The expression product is confirmed to be γ-hANP by the fact that γ-hANP prepared from human atrium cordis migrates to a site the same as the expression product on SDS polyacrylamide gel electrophoresis under the same condition. In the SDS polyacrylamide gel electrophoresis, a standard protein kit for determination of the mclecular weight supplied by Pharmacia P-L Biochemicals was used.

EXAMPLE 2

Preparation of γ-hANP from human atrium cordis 377 g of human atrium cordis was removed and boiled in ten volumes of 1 M acetic acid aqueous solution for 10 minutes, to inactivate protease present in the atrium cordis. The boiled atrium cordis in the acetic acid solution was then cooled to 4° C, added with cooled acetone to two volumes and homogenized with a Polytron homogenizer to extract the γ-hANP. The homogenate thus obtained was centrifuged at 16000 XG for 30 minutes to obtain a supernatant. From the supernatant, acetone was removed by vacuum distillation to obtain 150 ml of an extract containing γ-hANP.

To the extract water was added to 1l of total volume, and the diluted extract was subjected to reverse column chromatography using 90 ml of LCSORB SP-C-ODS column (Chemco). The charged column was washed with 450 ml of 0.1 N acetic acid solution, and eluted with 450 ml of a mixed eluent of water: acetonitrile: 10% trifluoroacetic acid (40:60:1). The elute was fractionated to a green fraction at an early stage and a brown fraction at a later stage. 225 ml of the green fraction was then lyophilized to obtain 90 mg of dried residue.

Figure 14:
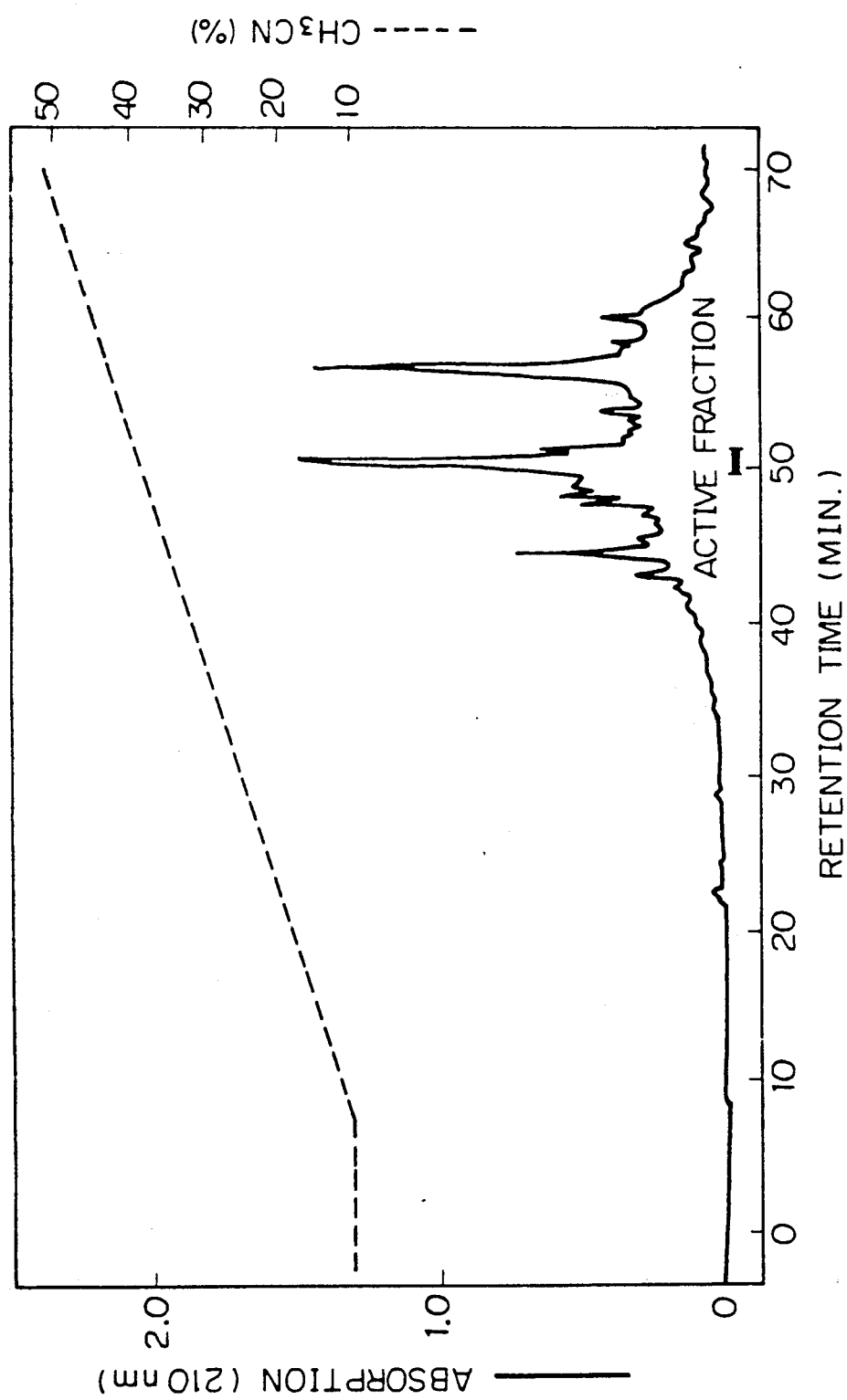
FIG. 14 represents an elution profile of a high performance liquid chromatography (HPLC) during the purification of the γ-hANP.
Figure 15:
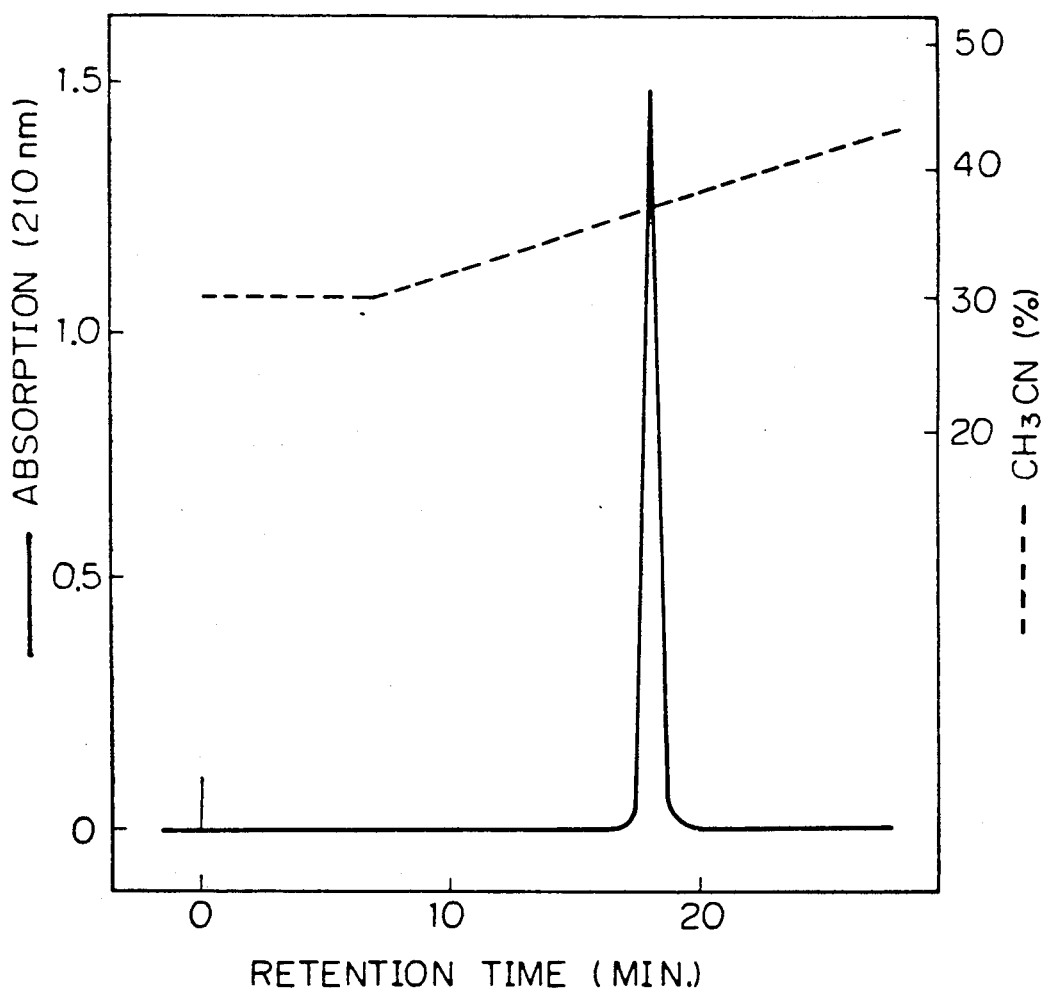
FIG. 15 represents an elution profile of HPLC of purified γ-hANP.

The residue thus obtained was dissolved in 5 ml of 1 N acetic acid, and the solution was subjected to gel filtration using a Sephadex G-75 column (Pharmacia, 1.8 > 135 cm) equilibrated with a 1 N acetic acid solution. The elution was carried out with 1 N acetic acid, and 5 ml of fractions were obtained. The elution profile is set forth in FIG. 13. Fractions No. 39 to 44 having chicken rectum relaxation activity were combined, and the combined fraction was subjected to HPLC using a TSK ODS column (Toyo Soda, 4.0 × 250 mm) and two eluents, i.e., (A) a mixture of water: acetonitrile: 10% trifluoroacetic acid (90:10:1) and (B) a mixture of water: acetonitrile: 10% acetic acid (40:60:1). The column was equilibrated with eluent (A), and 250 μl of the active fraction obtained from the Sephadex G-75 column was applied to the column. Elution was carried out by linear gradient from (A) to (B) at a flow rate of 1.0 ml/min and at a pressure of 110 to 130 Kg/cm$^2$ for 80 minutes. The result is set forth in FIG. 14. A peak fraction having chick rectum relaxation activity (retention time 50 minutes) was obtained, and subjected to HPLC using the same column. Elution was carried out using an eluent (A) water: acetonitrile: 10% trifluoroacetic acid (70:30:1) and an eluent (B) water: acetonitrile: 10% trifluoroacetic acid (40:60:1) in the same manner as described above. The result is set forth in FIG. 15. The main peak was fractionated to obtain about 3.37 nmole of purified γ-hANP for one run. The same procedure was repeated to obtain 404 n mole of γ-hANP.

EXAMPLE 3

Preparation of parenteral composition

| A) Injection solution | |
|---|---|
| Composition | |
| γ-hANP | 2 g |
| sodium chloride | 8 g |
| ascorbic acid | 2 g |
| sterile water | 1 l |

Method

γ-hANP and sodium chloride were dissolved in sterile water, an ampule was filled with 5 ml of the solution, and the ampule was then sealed.

| B) Lyophilizate | |
|---|---|
| Composition | |
| γ-hANP | 2 g |
| sorbitol | 20 g |

Method

γ-hANP and sorbitol were dissolved in 200 ml of sterile water, a vial was filled with 1 ml of the solution, and lyophilized, and the vial was then sealed.

The composition is dissolved in 5 ml of sterile water before parenteral administration.

We claim:

1. A process for production of a peptide comprising the following amino acid sequence:

X—Asn Pro Met Tyr Asn Ala Val Ser Asn Ala

Asp Leu Met Asp Phe Lys Asn Leu Leu Asp

His Leu Glu Glu Lys Met Pro Leu Glu Asp

Glu Val Val Pro Pro Gln Val Leu Ser Glu

Pro Asn Glu Glu Ala Gly Ala Ala Leu Ser

Pro Leu Pro Glu Val Pro Pro Trp Thr Gly

Glu Val Ser Pro Ala Gln Arg Asp Gly Gly

Ala Leu Gly Arg Gly Pro Trp Asp Ser Ser

Asp Arg Ser Ala Leu Leu Lys Ser Lys Leu

Arg Ala Leu Leu Thr Ala Pro Arg Ser Leu

Arg Arg Ser Ser Cys Phe Gly Gly Arg Met

Asp Arg Ile Gly Ala Gln Ser Gly Leu Gly

Cys Asn Ser Phe Arg Tyr.

wherein X is absent or represents the following amino acid sequence:

Met Ser Ser Phe Ser Thr Thr Thr Val Ser

Phe Leu Leu Leu Leu Ala Phe Gln Leu Leu

Gly Gln Thr Arg Ala.

comprising culturing *Escherichia coli* transformed with a plasmid containing a promoter region, SD sequence, and a DNA fragment comprising a nucleotide sequence coding for the peptide operatively linked in that order, to form the peptide, and recovering the peptide.

2. A DNA fragment in isolated form comprising a nucleotide sequence coding for a peptide consisting of the following amino acid sequence:

X—Asn Pro Met Tyr Asn Ala Val Ser Asn Ala

Asp Leu Met Asp Phe Lys Asn Leu Leu Asp

His Leu Glu Glu Lys Met Pro Leu Glu Asp

Glu Val Val Pro Pro Gln Val Leu Ser Glu

Pro Asn Glu Glu Ala Gly Ala Ala Leu Ser

Pro Leu Pro Glu Val Pro Pro Trp Thr Gly

Glu Val Ser Pro Ala Gln Arg Asp Gly Gly

Ala Leu Gly Arg Gly Pro Trp Asp Ser Ser

Asp Arg Ser Ala Leu Leu Lys Ser Lys Leu

Arg Ala Leu Leu Thr Ala Pro Arg Ser Leu

Arg Arg Ser Ser Cys Phe Gly Gly Arg Met

Asp Arg Ile Gly Ala Gln Ser Gly Leu Gly

Cys Asn Ser Phe Arg Tyr.

wherein X is absent or represents the following amino acid sequence:

Met Ser Ser Phe Ser Thr Thr Thr Val Ser

Phe Leu Leu Leu Leu Ala Phe Gln Leu Leu

Gly Gln Thr Arg Ala.

3. A DNA fragment in isolated form comprising a nucleotide sequence coding for a peptide consisting of the following amino acid sequence:

X—Asn Pro Met Tyr Asn Ala Val Ser Asn Ala

Asp Leu Met Asp Phe Lys Asn Leu Leu Asp

His Leu Glu Glu Lys Met Pro Leu Glu Asp

Glu Val Val Pro Pro Gln Val Leu Ser Glu

Pro Asn Glu Glu Ala Gly Ala Ala Leu Ser

Pro Leu Pro Glu Val Pro Pro Trp Thr Gly

Glu Val Ser Pro Ala Gln Arg Asp Gly Gly

Ala Leu Gly Arg Gly Pro Trp Asp Ser Ser

Asp Arg Ser Ala Leu Leu Lys Ser Lys Leu

Arg Ala Leu Leu Thr Ala Pro Arg Ser Leu

Arg Arg Ser Ser Cys Phe Gly Gly Arg Met

Asp Arg Ile Gly Ala Gln Ser Gly Leu Gly

Cys Asn Ser Phe Arg Tyr.

wherein X represents the following amino acid sequence:

Met Ser Ser Phe Ser Thr Thr Thr Val Ser

Phe Leu Leu Leu Leu Ala Phe Gln Leu Leu

Gly Gln Thr Arg Ala.

4. A DNA fragment in isolated form comprising a nucleotide sequence coding for a peptide consisting of the following amino acid sequence:

X—Asn Pro Met Tyr Asn Ala Val Ser Asn Ala

Asp Leu Met Asp Phe Lys Asn Leu Leu Asp

His Leu Glu Glu Lys Met Pro Leu Glu Asp

Glu Val Val Pro Pro Gln Val Leu Ser Glu

Pro Asn Glu Glu Ala Gly Ala Ala Leu Ser

Pro Leu Pro Glu Val Pro Pro Trp Thr Gly

Glu Val Ser Pro Ala Gln Arg Asp Gly Gly

Ala Leu Gly Arg Gly Pro Trp Asp Ser Ser

Asp Arg Ser Ala Leu Leu Lys Ser Lys Leu

Arg Ala Leu Leu Thr Ala Pro Arg Ser Leu

-continued

Arg Arg Ser Ser Cys Phe Gly Gly Arg Met

Asp Arg Ile Gly Ala Gln Ser Gly Leu Gly

Cys Asn Ser Phe Arg Tyr.

wherein X is absent.

5. A microbial host transformed with a plasmid containing the DNA fragment of claim 4.

6. A DNA fragment according to claim 2, wherein the nucleotide sequence comprises the following sequence:

Y-AAT CCC ATG TAC AAT GCC GTG TCC AAC GCA

GAC CTG ATG GAT TTC AAG AAT TTG CTG GAC

CAT TTG GAA GAA AAG ATG CCT TTA GAA GAT

GAG GTC GTG CCC CCA CAA GTG CTC AGT GAG

CCG AAT GAA GAA GCG GGG GCT GCT CTC AGC

CCC CTC CCT GAG GTG CCT CCC TGG ACC GGG

GAA GTC AGC CCA GCC CAG AGA GAT GGA GGT

GCC CTC GGG CGG GGC CCC TGG GAC TCC TCT

GAT CGA TCT GCC CTC CT A AAA AGC AAG CTG

AGG GCG CTG CTC ACT GCC CCT CGG AGC CTG

CGG AGA TCC AGC TGC TTC GGG GGC AGG ATG

GAC AGG ATT GGA GCC CAG AGC GGA CTG GGC

TGT AAC AGC TTC CGG TAC.

wherein Y is absent or represents the following nucleotide sequence:

ATG AGC TCC TTC TCC ACC ACC ACC GTG AGC

TTC CTC CTT TTA CTG GCA TTC CAG CTC CTA

GGT CAG ACC AGA GCT

7. A DNA fragment according to claim 2, wherein the DNA fragment is cDNA prepared by using mRNA as a template, which mRNA is obtained from human atrium cordis.

8. A plasmid containing a promoter region, SD sequence, and a DNA fragment according to claim 2, operatively linked in this order.

9. A plasmid according to claim 8, wherein the promoter is a λP$_L$ promoter.

10. A plasmid according to claim 8, wherein the SD sequence is an SD sequence of a CII gene, SD sequence of an lpp gene or SD sequence of an MS2A gene.

11. A plasmid according to claim 8, wherein the plasmid is pS220, pS223-3, or pS224-3.

12. Escherichia coli transformed with a plasmid according to claim 8.

13. A peptide in isolated form comprising the following amino acid sequence:

X—Asn Pro Met Tyr Asn Ala Val Ser Asn Ala

Asp Leu Met Asp Phe Lys Asn Leu Leu Asp

His Leu Glu Glu Lys Met Pro Leu Glu Asp

-continued

Glu Val Val Pro Pro Gln Val Leu Ser Glu

Pro Asn Glu Glu Ala Gly Ala Ala Leu Ser

Pro Leu Pro Glu Val Pro Pro Trp Thr Gly

Glu Val Ser Pro Ala Gln Arg Asp Gly Gly

Ala Leu Gly Arg Gly Pro Trp Asp Ser Ser

Asp Arg Ser Ala Leu Leu Lys Ser Lys Leu

Arg Ala Leu Leu Thr Ala Pro Arg Ser Leu

Arg Arg Ser Ser Cys Phe Gly Gly Arg Met

Asp Arg Ile Gly Ala Gln Ser Gly Leu Gly

Cys Asn Ser Phe Arg Tyr.

wherein X is absent or represents the following amino acid sequence:

Met Ser Ser Phe Ser Thr Thr Thr Val Ser

Phe Leu Leu Leu Leu Ala Phe Gln Leu Leu

Gly Gln Thr Arg Ala;

and pharmaceutically acceptable acid addition salts thereof.

14. A diuretic composition comprising a diuretic effective amount of a peptide gamma-hANP having the following amino acid sequence:

X—Asn Pro Met Tyr Asn Ala Val Ser Asn Ala

Asp Leu Met Asp Phe Lys Asn Leu Leu Asp

His Leu Glu Glu Lys Met Pro Leu Glu Asp

Glu Val Val Pro Pro Gln Val Leu Ser Glu

Pro Asn Glu Glu Ala Gly Ala Ala Leu Ser

Pro Leu Pro Glu Val Pro Pro Trp Thr Gly

Glu Val Ser Pro Ala Gln Arg Asp Gly Gly

Ala Leu Gly Arg Gly Pro Trp Asp Ser Ser

Asp Arg Ser Ala Leu Leu Lys Ser Lys Leu

Arg Ala Leu Leu Thr Ala Pro Arg Ser Leu

Arg Arg Ser Ser Cys Phe Gly Gly Arg Met

Asp Arg Ile Gly Ala Gln Ser Gly Leu Gly

Cys Asn Ser Phe Arg Tyr, wherein X is absent; or a pharmaceutically acceptable acid addition salt thereof and a pharmaceutically acceptable additive.

15. The diuretic composition according to claim 14, wherein the composition is a solution for parenteral administration and the pharmaceutically acceptable additive is a buffer, an osmotic pressure adjusting agent, a preservative or a combination thereof.

16. The diuretic composition according to claim 15, wherein the composition is a solution for parenteral administration and contains about 0.000005 to 5% of the gammahANP.

17. The diuretic composition according to claim 14, wherein the composition is in lyophilized form.

18. A hypotensor composition comprising a hypotensor effective amount of a peptide gamma-hANP having the following amino acid sequence:

X—Asn Pro Met Tyr Asn Ala Val Ser Asn Ala

Asp Leu Met Asp Phe Lys Asn Leu Leu Asp

His Leu Glu Glu Lys Met Pro Leu Glu Asp

Glu Val Val Pro Pro Gln Val Leu Ser Glu

Pro Asn Glu Glu Ala Gly Ala Ala Leu Ser

Pro Leu Pro Glu Val Pro Pro Trp Thr Gly

Glu Val Ser Pro Ala Gln Arg Asp Gly Gly

Ala Leu Gly Arg Gly Pro Trp Asp Ser Ser

Asp Arg Ser Ala Leu Leu Lys Ser Lys Leu

Arg Ala Leu Leu Thr Ala Pro Arg Ser Leu

Arg Arg Ser Ser Cys Phe Gly Gly Arg Met

Asp Arg Ile Gly Ala Gln Ser Gly Leu Gly

Cys Asn Ser Phe Arg Tyr.

wherein X is absent; or a pharmaceutically acceptable acid addition salt thereof and a pharmaceutically acceptable additive.

19. A hypotensor composition according to claim 18, wherein the composition is a solution for parenteral administration and the additive is a buffer, an osmotic pressure adjusting agent or a preservative, or a combination thereof.

20. A hypotensor composition according to claim 18, wherein the composition is a solution for parenteral administration and contains about 0.000005 to 5% of the gammahANP.

21. A hypotensor composition according to claim 18, wherein the composition is in a lyophilized form.

* * * * *